United States Patent [19]

Hofstee

[11] 4,000,098

[45] Dec. 28, 1976

[54] SEPARATION OF PROTEINS BY HYDROPHOBIC ADSORPTION

[75] Inventor: Barend H. J. Hofstee, Palo Alto, Calif.

[73] Assignee: Palo Alto Medical Research Foundation, Palo Alto, Calif.

[22] Filed: Sept. 10, 1974

[21] Appl. No.: 504,754

Related U.S. Application Data

[63] Continuation-in-part of Ser. No. 497,875, Aug. 16, 1974, abandoned.

[52] U.S. Cl. ..................... 260/8; 195/63; 195/66 R; 195/68; 195/127; 195/DIG. 11; 210/24; 260/112 R

[51] Int. Cl.² ......................... C07G 7/00

[58] Field of Search .......... 260/8, 112 R; 195/66 R, 195/127, 146

[56] References Cited

UNITED STATES PATENTS

| | | | |
|---|---|---|---|
| 3,562,289 | 2/1971 | Battista et al. | 260/309 |
| 3,705,084 | 12/1972 | Reynolds | 195/63 |

OTHER PUBLICATIONS

El-el, et al., "Hydrocarbon – Coated Sepharoses;" Bio–Chem. and Biophys. Res. Comm. vol. 49, No. 2, 1972(pp. 383–390).

Yon; R. J., "Enzyme Purification by Hydrophobic Chromatography" Bio–Chem. J., vol. 137, Jan. 1974(pp. 127–130).

Hofstee; B. H. J., "Protein Bonding by Agarose Carrying Hydrophobic Groups in Conjunction with Charges;" Bio–Chem. and Biophys., Res. Comm., vol. 50 No. 3, Feb. 1973 (pp. 751–757).

Zaborsky; O., "Immobilized Enzymes" CRC Press; Cleveland, Ohio, May 1973, (pp.75–82).

C.A. 75:118613d, "Adsorbents for Chromatographic Protein Separation," Fryklund et al., 1971.

C.A. 78:133023s, "Hydrophobic Affinity Chromatography of Proteins," Hofstee, 1973.

*Primary Examiner*—Edward M. Woodberry
*Attorney, Agent, or Firm*—Edward B. Gregg; Julian Caplan

[57] ABSTRACT

Separation of proteins from one another by passing an aqueous solution of a mixture of proteins through two or more bodies of matrices each having hydrophobic ligands covalently attached to it, the order of hydrophobicity being such that the protein mixture comes into contact with a first body having the least hydrophobic ligands, then with a second body having more hydrophobic ligands, etc., whereby the most highly hydrophobic proteins are adsorbed on the first (least hydrophobic) matrix, etc. in order of increasing hydrophobicity of the matrices and decreasing hydrophobicity of the proteins in the mixture.

3 Claims, 1 Drawing Figure

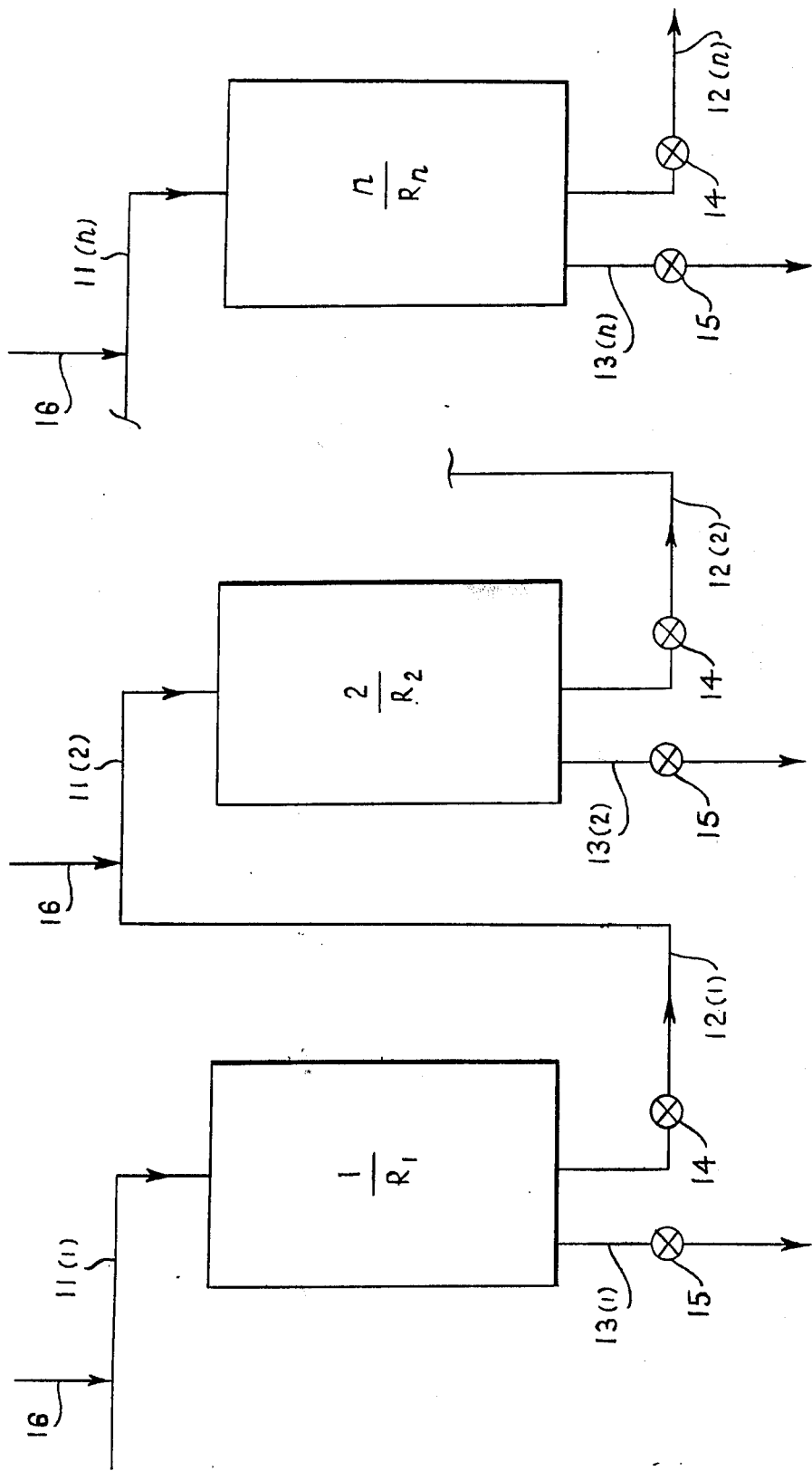

SEPARATION OF PROTEINS BY HYDROPHOBIC ADSORPTION

This application is a continuation-in-part of my copending application Ser. No. 497,875 filed Aug. 16, 1974, and now abandoned entitled "Immobilized Enzymes and Method of and Reactors for Carrying Enzymatic Reactions Employing Same".

Proteins are presently separated from mixtures such as mixtures of gamma globulins and albumin derived from blood plasma by such techniques as ion exchange and the use of molecular sieves. Such methods depend upon electric charges and molecular size.

It is an object of the present invention to provide alternative methods and apparatus for separating proteins which have advantages over previous methods and/or supplement previous methods.

It is a further and particular object of the invention to provide a method and apparatus whereby proteins can be readily separated from one another by adsorptive means which is effective, which is mild, which does not denature the proteins and which can be made to release the proteins by mild means.

The above and other objects of the invention will be apparent from the ensuing description and the appended claims.

I have discovered that proteins can be separated one from another by utilizing their hydrophobic characteristics, by providing a series of adsorbent bodies differing in hydrophobicity, and by passing the protein mixture in aqueous solution through a series of such adsorbent bodies arranged in increasing order of hydrophobicity.

By this means I have discovered that a protein mixture is fractionated in order of hydrophobicity with each succeeding fraction being adsorbed on a body of matrix that is more hydrophobic than the preceding body of matrix.

By "hydrophobicity" is meant the tendency of a given protein to bond adsorptively to hydrophobic sites on a hydrophobic adsorbent body. It is now known that proteins, including enzymes, have exposed hydrophobic sites on their three dimensional structures due to hydrophobic groups such as the methyl group of alanine, the isopropyl group of valine, the isobutyl group of leucine, and the benzyl group of phenyl alanine. As described in my co-pending application above mentioned, Ser. No. 497,875, it is known that such sites on an enzyme will bind adsorptively to hydrophobic ligands on a matrix such as activated agarose covalently bonded to alkylamines such as n-hexylamine; that such bonding is reversible by the use of a modified eluant such as ethylene glycol-aqueous salt solution; and that the mild (but stable) adsorptive binding and mild (but effective) conditions of elution are compatible with retention of activity of the enzyme. That is, the class of enzymes (which are proteins) is stably enough bound to such a matrix to be insolubilized and immobilized; the binding does not destroy or greatly inhibit activity of the enzyme; and the enzyme can be recovered by elution without destroying or greatly inhibiting its activity.

I have now extended these discoveries to the separation of proteins from mixtures thereof such as, for example, separating gamma globulins from albumin in blood serum; and I have done so by taking advantage of the differing hydrophobic characteristics of such proteins. Such procedure is illustrated in the accompanying drawing.

Referring to the single FIGURE of the drawing, a series of vessels numbered 1 through $n$ in sequence are shown. An aqueous solution of a mixture of proteins is introduced. Each vessel contains a matrix designated as $R_1, R_2 \cdots R_n$.

The hydrophobicities of the matrices rank as follows: $R_1 < R_2 < R_3 \cdots R_{n-1} < R_n$. That is to say, a gradient of hydrophobicities is employed ranging from a highest hydrophobicity to a lowest hydrophobicity. Examples of such matrices are given below. Such matrices are solid and water insoluble and they are particulate or in any event they are sufficiently porous that a solution may pass through and interfacial contact of solution and matrix is promoted. An aqueous solution of protein enters vessel No. 1 through a line 11 and passes out through a line 12 (1) to vessel No. 2, etc. Solution leaves the system through line 12 ($n$). Each vessel is provided with a separate outlet line 13 (1), 13 (2), etc. Each of the lines 12 (1), etc. and each of the lines 13 (1) etc. is provided with a valve 14 or 15, respectively.

In passing through vessel 1, a protein or a fraction of proteins which is the most highly hydrophobic is adsorbed on matrix $R_1$ owing to the fact that matrix $R_1$ is the least hydrophobic, hence it adsorbs only the most highly hydrophobic protein or protein fraction. The remaining, less hydrophobic proteins pass through with no binding or with relatively little binding. In each vessel a protein or a fraction of proteins is adsorbed according to a function of $H_m$ (hydrophobicity of the matrix) and $H_p$ (hydrophobicity of the particular protein or protein fraction).

At a suitable time, the throughput of protein solution is terminated by closing the valves 14 and the valves 15 are then opened. A suitable eluant such as an ethylene glycol-aqueous salt solution is then passed through each vessel by introducing it through a branch line 16. The eluant (which may be the same for all the vessels or may be different for different vessels) will elute the protein or protein fraction adsorbed in each vessel. The eluant may be treated in any manner. For example some or all of the fractions may be subjected to ion exchange or molecular sieve treatment. If a dry product is desired the solution may be lyophilized.

Separated fractions may be further fractionated by repetition of the same procedure aided by employing matrices having hydrophobicities that are closer together. The method of the present invention may be combined with other methods such as ion exchange or molecular sieve treatment.

The matrices $R_1, R_2$, etc. may be prepared by any suitable means, preferably in the manner described in my copending application, as follows: A substance such as agarose activated by means of CNBr is covalently bonded to a multiplicity of hydrophobic ligands which are capable of bonding adsorptively with hydrophobic sites on a protein. The thus modified matrix may be represented as Matrix -X-R in which there are multiple -X-R groups attached covalently to the matrix; R is a hydrophobic group, and X is a hetero atom or group of atoms that serve to bond R to the matrix. R is typically a hydrocarbon (aromatic, aliphatic or mixed aromaticaliphatic) group. X is a hetero atom, e.g., O or S, or group of atoms, e.g., NH, which may also carry an electric charge in the form of an ion.

In rough order of hydrophobicity various ligands may be described as follows: In the straight chain [alkyl] series $CH_3$ to $C_nH_{2n+1}$, hydrophobicity increases with the value of $n$, but this criterion is limited by the fact that higher alkyl groups have a detergent effect which may denature the proteins; branched chain alkyl groups are less hydrophilic as a group than straight chain alkyl groups; the introduction of unsaturation, e.g., an olefinic bond or of a hydrophilic functional group diminishes hydrophobicity; aromatic hydrocarbon groups are hydrophobic and their hydrophobicity is enhanced by the presence of alkyl groups either as linking groups as in the case of benzyl or as ring substituents on aromatic groups directly bonded to the matrix, as in the case of methyl phenyl.

These hydrophobic groups or ligands (generally designated as R) are attached to a substance called herein for convenience "the matrix". The substance used to introduce the ligand is called for convenience "the modifier" and the resulting product is called "the modified matrix". Matrices include activated agarose [see Porath Nature 215, 1491 (1967) and Cuatrecasas, J. Biol. Chem. 245, 3059, (1970)]. Also cellulose, polystyrene, agarose, polyacrylamide and starch among organic substances and charcoal, glass beads and ceramic materials among inorganic substances may be used. See for example, Zaborsky "Immobilized Enzymes" CRC Press, 1973, Table IV on pages 28–46 for a list of suitable matrices (listed under the heading "Parent Polymer"). In general, any matrix may be used which is compatible with protein separations, which is water insoluble, which is hydrophilic and which can be modified by covalent linkage to form hydrophobic ligand groups -X-R.

Modifiers include a wide variety of substances, e.g., primary and secondary amines $R-NH_2$ and $R-NHR_1$ ($R_1$ = hydrocarbon group), alcohols ROH, acyl halides RCOY (Y = Cl, Br) acid anhydrides

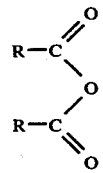

(R's the same or different) etc. which will react with chemically reactive groups on the matrix to form ligands R-X-. Examples of such modifiers (ligand sources) are the $C_1 - C_n$ primary n-alkyl amines ($n=1$, 2, 3 or 4 to 8 or higher), e.g., methyl amine, propyl amines (primary and secondary) and primary, secondary and tertiery butyl, pentyl, hexyl, heptyl, octyl, etc. amines; aryl amines such as aniline and ring alkyl substituted anilines; aralkyl amines such as benzylamine, mixed alkyl-aryl amines such as N-methyl aniline; also alcohols and mercaptans R-X-H (X is O or S) where R is any of the groups mentioned above; etc. Further examples of modifiers are hydrophobic amino acids such as valine, leucine, phenyl alanine and tryptophan.

In certain instances it may be necessary to activate the matrix so that it will react with the modifier to produce the ligands -X-R. Therefore, in the generalized representation (matrix -X-R) it is to be understood that if the source material for the matrix, for example agarose, is not itself amenable to reaction with ligand sources or modifiers it is conditioned or activated so that it will be amenable to such reactions. An An example is the activation of agarose by treatment with cyanogen halide as described, for example, by Porath et al. in Nature, 215, 1491 (1967) and by Cuatrescasas in J. Biol. Chem. 245, 3059 (1970).

As yet no generally accepted scale or measure of hydrophobicity of either ligands or proteins is available as far as I know. However, the ranking of modified matrices and of proteins with regard to hydrophobicity can be readily determined by experiment. For example, a protein mixture such as a mixture of blood albumin and gamma globulin may be employed and various modified matrices may be tested. For such purposes it is not necessary that quantitative separation of a mixture or quantitative adsorption of a single protein be achieved; it is sufficient of significant differences are observed whereby to rank matrices in order of increasing hydrophobicity. By the same means proteins may be ranked according to their decreasing hydrophobicities. Thus if a quantity of a given matrix such as activated agarose is covalently bonded to a more highly hydrophobic ligand such as n-hexylamine and another quantity of the same matrix is covalently bonded to a molecularly equivalent amount of a less highly hydrophobic ligand such as phenyl alanine, the relative adsorption of two proteins A and B on these matrices will reveal which is the more hydrophobic (hence more strongly adsorbed) and which is the less hydrophobic. In this instance the more highly hydrophobic protein will bond well to both modified matrices, whereas the less highly hydrophobic protein will bond well only to the matrix modified by n-hexylamine.

A further control over varying degrees of hydrophobicity is the degree of modification. Each ligand R is presumed to provide a hydrophobic site for adsorptive attachment to a hydrophobic site on a protein. Hence if the packing or density of ligands R is greater, it will bind to more sites on a given protein molecule, hence it will bind such protein more strongly than the same matrix with fewer and more widely separated ligands. More particularly, if the density of ligands R is such that the average distance between R's is less than the diameter of the protein molecule, a greatly enhanced adsorption will occur.

A further factor to be considered is the electrostatic effect. If the charge carried by a protein under conditions of separation (which may be determined as a matter of convenience or of necessity) is opposite to the charge on the modified matrix, the electrostatic effect is one of attraction and will promote binding, whereas if the charges on the matrix and on the protein are the same an electrostatic repulsion will result. The electrostatic effect can be modified and quenched by employing a high salt concentration, e.g., 3 molar NaCl. Such high salt concentrations enhance the hydrophobic effect which is especially useful when the charges on the modified matrix and the protein are the same.

Yet another effect to be considered is specific affinity such as the affinity of certain groups other than hydrophobic groups on the protein and the modified matrix or the fit between ligands on the modified matrix and cavities on the protein.

In the following examples, the matrix was agarose (Sepharose 4B of Pharmacia) activated by CNBr, according to the method described by Cuatrecasas in J. Biol. Chem. 245, 3059 (1970). Modifiers (sources of hydrophobic ligands) were n-hexylamine and phenyl alanine. The method used was as follows:

Two to five grams of the hexylamine-hydrochloride, recrystallized from ethanol by the addition of ethyl ether, were dissolved in 20–50 ml of 50% (v/v) dimethylformamide (DMF) in water. The pH of the mixture was adjusted to 10.2 (in which region the amine shows strong buffering capacity) and after cooling to about 5°, 20–30 ml settled slurry of agarose (Sepharose 4B, Pharmacia), activated with 4–6 grams of CNBr and washed with ice cold water, was added. The mixture was stirred overnight in the cold and the substituted agarose was washed exhaustively with 50% (v/v) DMF or ethylene glycol in 0.01 M Tris-HCl buffer, pH 8. The phenyl alanine substituted agarose was prepared in a similar manner.

EXAMPLE 1

Two columns were prepared. The first (less hydrophobic) column contained a bed of activated agarose modified by covalent attachment of phenyl alanine and the second (more hydrophobic) column contained a bed of agarose modified by covalent attachment of n-hexylamine. A mixture of bovine serum albumin (BSA) and gamma globulin was used. The mixture contained parts BSA and parts gamma globulin. Each column was equilibrated with 3.3 M NaCl at pH 8. The mixture of proteins in 3.3 M NaCl at pH 8 was passed first through column No. 1 (phenyl alanine modified activated agarose) and then through the column No. 2 (n-hexylamine modified activated agarose). The gamma globulin was adsorbed quantitatively by the first (less hydrophobic) column. The BSA passed through this column without substantial adsorption but was adsorbed quantitatively by column No. 2. Then by passing 50% aqueous ethylene glycol in one molar NaCl separately through each column, the adsorbed proteins were removed quantitatively without denaturing them.

EXAMPLE 2

Human blood plasma was passed through the same columns (after equilibration with 3.3 molar Nacl at pH 8). A separation occurs of more hydrophobic protein in the first column, less hydrophobic proteins in the second column.

I claim:

1. A method of separating two or more proteins from a mixture of proteins which comprises providing at least two bodies of hydrophobic adsorbent capable of adsorbing proteins by hydrophobic adsorption, said bodies having different hydrophobicities ranging from a lowest hydrophobicity to a highest hydrophobicity, and passing such protein mixture in aqueous solution through said bodies in order of increasing hydrophobicity whereby the proteins are bound to the bodies of adsorbent in order of hydrophobicities of the proteins ranging from a highest hydrophobicity to a lowest hydrophobicity.

2. The method of claim 1 wherein said bodies consist of matrices having hydrophobic ligands covalently attached thereto, the selection and/or density of such ligands controlling the hydrophobicity of each body.

3. Apparatus for adsorptive separation of proteins comprising a plurality of beds of adsorbent material each having the capacity to adsorptively bind to at least one protein, each bed having a hydrophobicity different from the hydrophobicity of the other beds, said beds being arranged in order of increasing hydrophobicity and being interconnected whereby when a solution containing a mixture of proteins passes through the beds they are preferentially adsorbed on successive beds in order of decreasing hydrophobicity.

* * * * *